US00PP15380P3

(12) United States Plant Patent
LaBonte et al.

(10) Patent No.: US PP15,380 P3
(45) Date of Patent: Nov. 30, 2004

(54) BIENVILLE SWEETPOTATO

(50) Latin Name: *Ipomoea batatas*
Varietal Denomination: Bienville

(75) Inventors: Don R. LaBonte, Baton Rouge, LA (US); James M. Cannon, Baton Rouge, LA (US); Christopher A. Clark, Baton Rouge, LA (US); Arthur Q. Villordon, Monroe, LA (US); Paul W. Wilson, Gonzales, LA (US); Abner H. Hammond, Baton Rouge, LA (US); Rick N. Story, Baton Rouge, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 77 days.

(21) Appl. No.: 10/158,425

(22) Filed: May 29, 2002

(65) Prior Publication Data

US 2003/0226185 P1 Dec. 4, 2003

(51) Int. Cl.[7] ..... A01H 5/00
(52) U.S. Cl. ..... Plt./258
(58) Field of Search ..... Plt./258

*Primary Examiner*—Kent Bell
(74) *Attorney, Agent, or Firm*—André J. Porter; John H. Runnels; Bonnie J. Davis

(57) ABSTRACT

A new variety of sweetpotato, identified as 'Bienville', is disclosed having superior disease resistance to both southern root-knot nematode and soil rot, and high yield characteristics.

3 Drawing Sheets

This invention pertains to a new and distinct variety of sweetpotato.

BACKGROUND OF THE INVENTION

Sweetpotatoes, unlike Irish potatoes (*Solanum tuberosum*), are not tuber propagated plants. A "tuber" is a short, thickened portion of an underground branch. Along a tuber are found "eyes," each of which comprises a ridge bearing a scale-like leaf (analogous to a branch leaf) having minute meristematic buds in the axial of the leaf. By contrast, sweetpotato roots are developmentally and anatomically true roots, lacking meristematic buds, and are not derived from an underground branch. Sweetpotatoes do not form tubers.

SUMMARY OF THE INVENTION

Genus and species name

This new and distinct sweetpotato variety, *Ipomoea batatas* (L.) Lam., which demonstrates superior southern root-knot nematode and soil-rot resistance, and high yield characteristics as compared to other available sweetpotato varieties known to the inventors.

Variety denomination

This new and distinct sweetpotato variety is identified as 'Bienville', and is characterized by its dark orange flesh and elliptical roots.

BRIEF DESCRIPTION OF THE DRAWINGS

The file of this patent contains at least one photograph executed in color. Copies of this patent or patent application publication with color drawing(s) will be provided by the Office upon request and payment of the necessary fee.

DETAILED BOTANICAL DESCRIPTION

This new variety of sweetpotato, identified as 'Bienville', resulted from an open pollinated cross to the Louisiana Agricultural Experiment Station female parent 'L86-33' (unpatented), which was performed in 1993. The male parent is unknown. No patented male parents were among potential pollen sources in the crossing nursery. 'Bienville' was developed by the Louisiana Agricultural Experiment Station in Baton Rouge, La., to provide a new variety with characteristics similar to 'Beauregard' (unpatented), but with improved resistance to southern root-knot nematode resistance. 'Bienville' is characterized by a darker orange flesh. The female parent 'L86-33' (unpatented) has similar disease resistance characteristics to that of 'Bienville', except for its intermediate resistance to southern root-knot nematode. 'Bienville' and 'L86-33' are distinguished by the colors of their vines. Specifically, 'Bienville' has green vines [7.5 G (green)Y (yellow) (5/6)], while 'L86-33' has purple vines [5 R (red) P (purple) (3/6)].

Color terminology used herein is in accordance with the MUNSELL® color charts for plant tissue and the MUNSELL® Book of Color for root skin and flesh determination (Munsell Color, Gretag Macbeth LLC, New Windsor, N.Y.). The color descriptions and color illustrations are as nearly true as is reasonably possible. However, it is understood that both color and other phenotypic expressions described herein may vary from plant to plant with differences in growth, environment and cultural conditions, without any change in the genotype of the variety 'Bienville'.

'Bienville' roots were stored during the winter at the Louisiana Agricultural Experiment Station (Sweetpotato Research Station) in Chase, La. During the following spring, 'Bienville' was planted and produced approximately 8–10 sprouts, which were cut and transplanted successfully for asexual reproduction. Asexual propagation of the new cultivar by cuttings at the location previously stated, has shown that the unique features of this new sweetpotato are stable, and the plant reproduces true to type in successive generations of asexual propagation. Plants described herein are approximately 90–110 days in age from planting in full sun field plantings.

Figure 1:
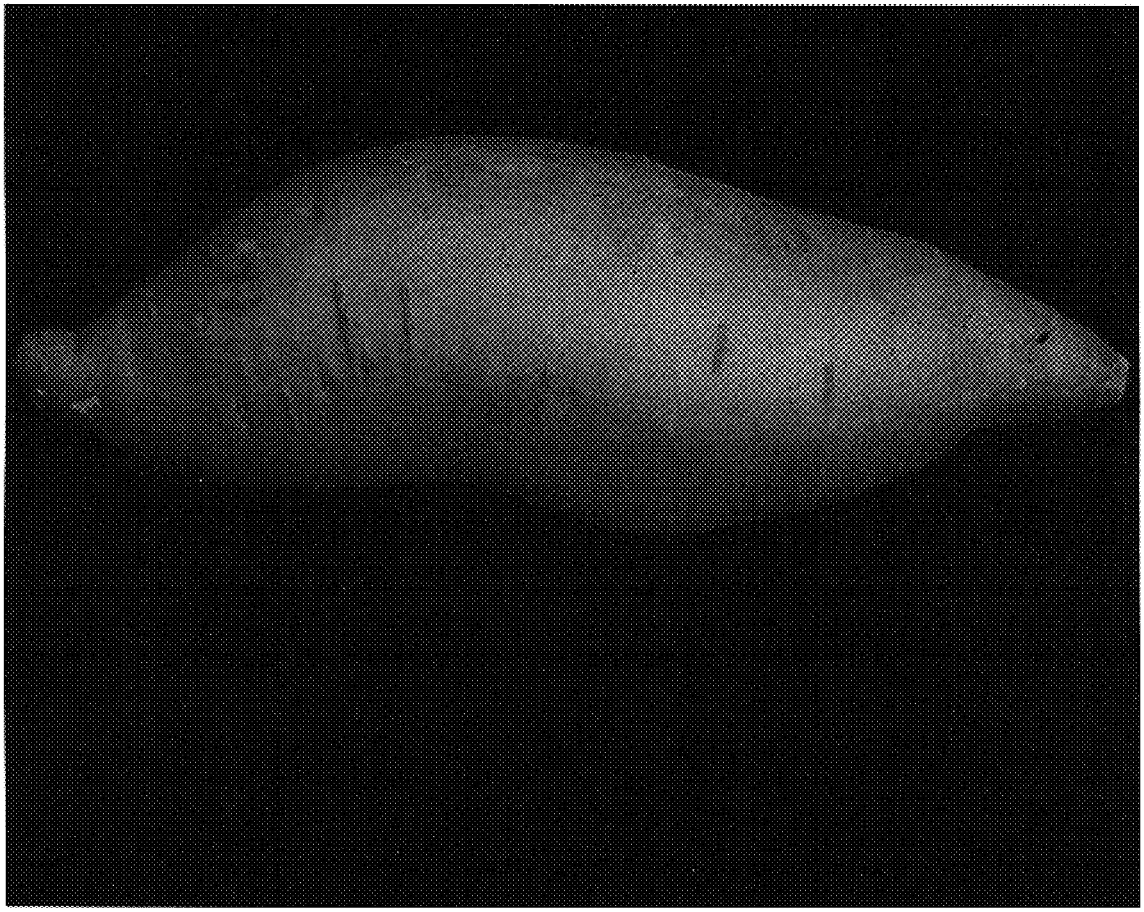
FIG. 1 is a color photograph of the fleshy root of the novel variety of sweetpotato identified as 'Bienville'.
Figure 2:
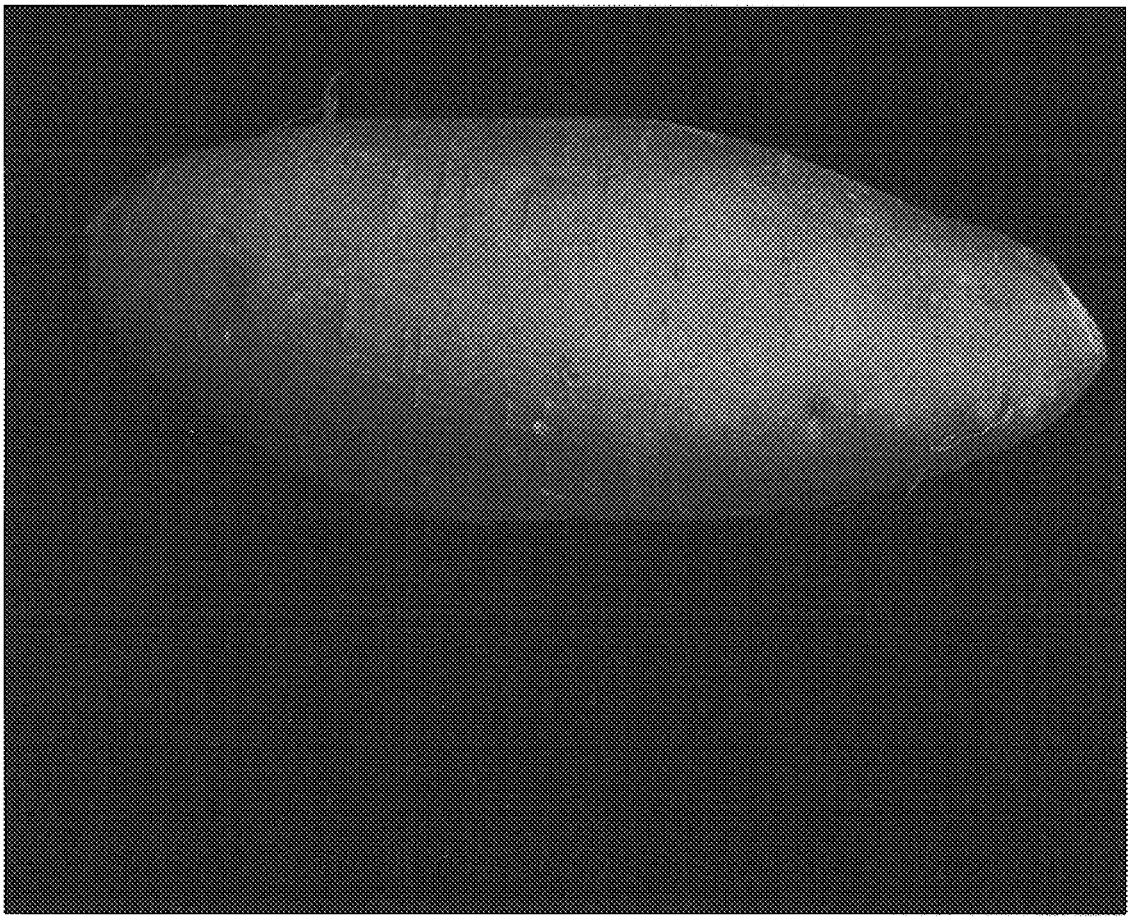
FIG. 2 is a color photograph of the fleshy root of the sweetpotato variety identified as 'Beauregard'.

FIG. 1 depicts the fleshy root form of the 'Bienville' sweetpotato. Skin varies in color from light to medium rose, and is typically lighter than 'Beauregard' at harvest and similar to 'Beauregard' after several months of storage. (Skin color lightens in storage). See 'Beauregard' as depicted in FIG. 2. Skin is smooth, similar to that of 'Beauregard'. Storage roots are elliptic and elongated without lobing, similar to 'Beauregard'. The cortex is 4–5 mm in depth. A typical fleshy root of 'Bienville' is 13–14 cm long and 6–7 cm wide. Roots are rounded at the proximal end (junction with the main root) and more acute at the distal end and weight 340 g. 'Beauregard' has similar dimensional characteristics.

Figure 3:
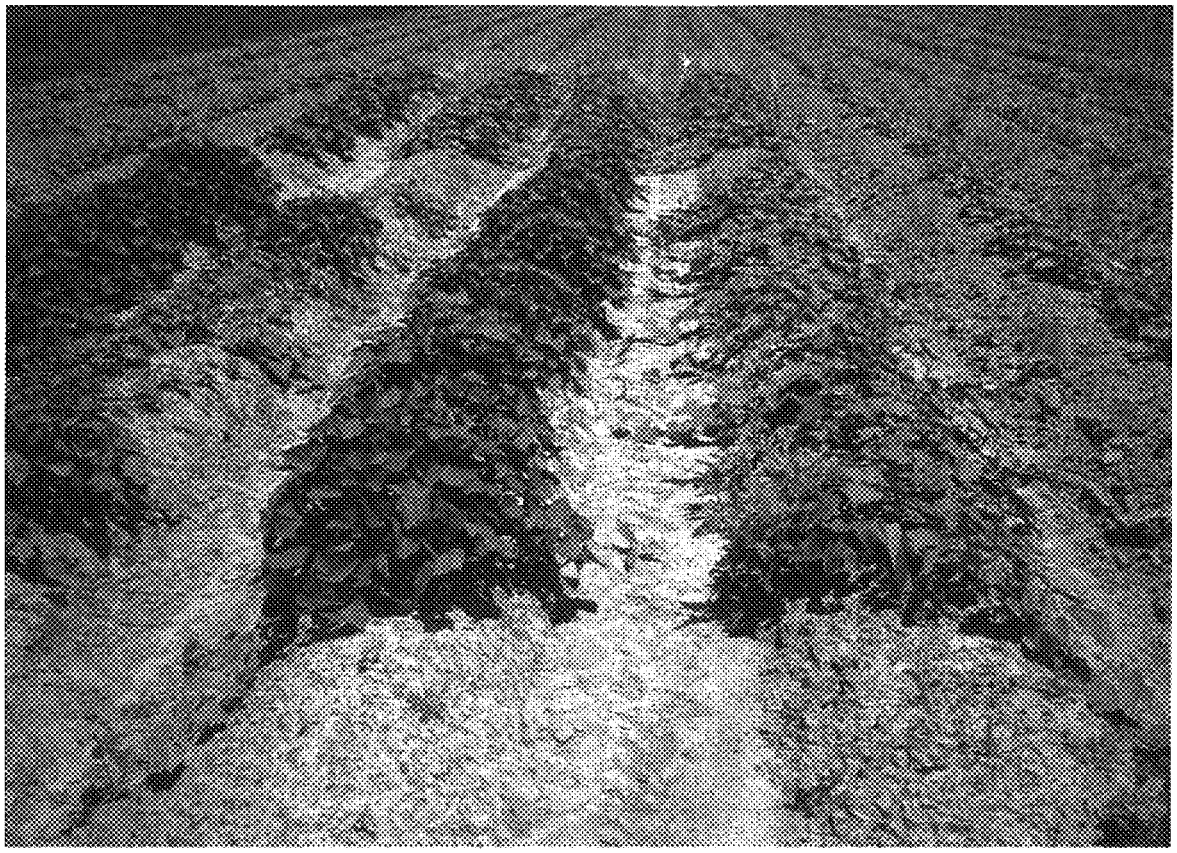
FIG. 3 is a color photograph of the canopy biomass of both the novel variety of sweetpotato identified as 'Bienville' (shown on the left side of the photograph) and the variety identified as 'Beauregard' (shown on the right side of the photograph).

FIG. 3 depicts the canopy biomass of the 'Bienville' sweetpotato. 'Bienville' has green-stemmed vines [7.5 G (green) Y (yellow) (5/6)] from the apex to the crown of the roots. The appearance of the canopy biomass is greater than 'Beauregard' and slightly more than another sweetpotato variety named 'Jewel' (unpatented; not shown). The canopy architecture is upright (32 cm in height from the soil surface) and erect prior to spreading (67.5 cm radius), while 'Beauregard' exhibits a prostrate growth habit. Between 2 to 3 main vines arise from the main stem near the soil surface. The main stem has a 2 cm diameter. The main vines have a length of 129 cm, a diameter of 0.5 cm at a distance of 65 cm from the base, and a diameter of 0.4 cm at the first internode of the first fully developed leaf from the apex. Between 4 to 5 lateral branches arise from each of the main vines. The length of the first internode from the apex between the first and the second fully developed leaves is 5 cm. The internode length for other sections of the vine average between 5 to 7 cm. Unfolded immature leaves are dark purple [5R (red) P (purple) (3/4)] for the upper and the lower surfaces, and gradually change (over one to two nodes from the apex) to a dark green upper surface [7.5 G (green) Y (yellow) (4/6)], and then to a green lower surface [5 G (green) Y (yellow) (4/4)]. Mature leaves which are located five nodes away from the apex have an acute apex, a cordate or hastate base, and a smooth leaf margin. Mature leaves have a length of 7.0 cm and a width of 7.5 cm. Abaxial and adaxial veins are dark purple [5R (red) P (purple) (3/4)]. The petiole changes from dark purple [5R (red) P (purple) (3/4)] near the leaf junction to green [7.5 G (green) Y (yellow) (5/6)], and then to purple [5 RP (4/8)] at the node. The petiole has a length of 9–10 cm at a distance of five nodes from the apex, and has a diameter of 4 mm at a distance of 5 cm from the leaf junction. The dormant nodal meristem is also purple [5 R (red) P (purple) (4/6)]. The mature leaves have green veins [5 G (green) Y (yellow) (6/6)] on the lower leaf surface.

A typical inflorescence of 'Bienville' has 7–8 flowers per peduncle. The peduncle is green [7.5 G (green) Y (yellow) (5/6)], and has a length of 16 cm and a diameter of 3 mm. The flower bud (one day before opening) has a length of 3 cm from the base of the calyx to the tip of the closed corolla and a maximum width of 0.6 cm. The closed corolla is a purple [5 R (red) P (purple) (5/6)]. Sepal color and size are similar to an opened flower (described more fully below). The individual flower buds have a length of 2.5–3 cm long by 8 mm wide. The individual open flowers have a length of 5 cm from the base of the calyx (calyx is 0.6 cm wide). The fused flower petals form a corolla (3 to 4 cm wide at the apex) and are in a pentagonal pattern with a smooth edge. The inner throat of the corolla is purple [5 R (red) P (purple) (4/8)], but changes to a lighter purple [5 R (red) P (purple) (7/4)] at the outer surface. The inner and outer limb of the corolla (corollas outermost area, distal from the calyx) is a very light purple [5 R (red) P (purple) (8/2)]. The five sepals forming the calyx are green [7.5 G (green) Y (yellow) (5/6)], and have an elliptic shape with a cordate apex. The length and width of the sepal is 7 mm and 4 mm, respectively. The sepal margins are smooth. The stigma is purple [5 R (red) P (purple) (8/2)], and has a length of 1.5 cm. Five stamens are attached to the ovary, but are inferior to the stigma.

Colorimetric evaluations using the MUNSELL® Book of Color for root skin and flesh determination (Munsell Color, GretagMacbeth LLC, New Windsor, N.Y.) for both 'Bienville' and 'Beaurgard' storage roots at harvest, are shown in Table 1.

TABLE 1

| | Cultivar | Color[2] |
|---|---|---|
| Skin | 'Bienville' | 10.0 R (red) (5/6) |
| | 'Beauregard' | 7.5 R (red) (5/6) |
| Cortex | 'Bienville' | 5 Y (yellow) R (red) (8/8) |
| | 'Beauregard' | 5 Y (yellow) R (red) (8/6) |
| Flesh | 'Bienville' | 2.5 Y (yellow) R (red) (7/12) |
| | 'Beauregard' | 2.5 Y (yellow) R (red) (7/10) |

[2]Data represent color scale values using the MUNSELL ® Book of Color, color-order system.

EXAMPLE 1

Tests Conducted

To confirm that 'Bienville' was a new variety, controlled tests (e.g., pathogen responses and yield) were conducted at the Louisiana Agricultural Experiment Station in Baton Rouge, La. 'Beauregard' was selected for comparison tests with 'Bienville' because of its commercial dominance in the United States sweetpotato acreage. 'Beauregard' occupies more than 70% of the acreage devoted to sweetpotatoes in the United States. Diseases that commonly affect the growth of sweetpotatoes were selected to test for pathogen responses in both varieties. Scions of 'Bienville' and 'Beauregard' reacted similarly to most diseases evaluated in the controlled tests. 'Bienville' was resistant to soil rot caused by *Streptomyces ipomoeae* (Person & W. J. Martin) Waksman & Henrici. In severely infested fields, yield of 'Bienville' was unaffected, and had storage roots with few lesions. While yield of 'Beauregard' was also unaffected, storage roots often had lesions. 'Bienville' and 'Bearegard' exhibited similar resistance to Fusarium wilt or stem rot caused by *Fusarium oxysporum* Schlect. f. sp. *batatas* (Wollenw.) Snyd. & Hans.

Nematode reproduction was measured in greenhouse tests. 'Bienville' exhibited higher resistance to southern root-knot nematode, *Meloidogyne incognita* (Kofoid & White 1919) Chitwood 1949 races 1 and 3, than 'Beauregard'. 'Bienville' and 'Beauregard' were both resistant to the development of internal cork, a disease presumably caused by a virus (unknown), but some storage roots developed an unusual discoloration of the vascular ring at the proximal end. 'Bienville' and 'Beauregard' exhibited similar resistance to Fusarium root rot caused by *Fusarium solani* (Sacc.) Mart. emend. Snyd. & Hans. At harvest, 'Bienville' was more resistant to bacterial soft rot caused by *Erwinia chrysanthemi* Burkholder, McFadden & Dimock, than 'Beauregard'. However, 'Bienville' exhibited susceptibility to bacterial soft rot comparable to that of 'Beauregard' after storage for three to five months. 'Bienville' and 'Beauregard' were both resistant to Rhizopus soft rot caused by *Rhizopus stolonifer* (Ehr. ex. Fr.) Lind. 'Bienville' and 'Beauregard' exhibited a similar incidence of circular spot caused by *Sclerotium rolfsii* Sacc.

'Bienville' did not appear to show any novel insect resistance. 'Bienville' and 'Beauregard' showed similar levels of susceptibility to important insect pests, notably the banded cucumber beetle, *Diabrotica balteata* LeConte, white grub, *Plectris aliena* Chapin or Phyllophaga spp., and the sweetpotato weevil, *Cylas formicarius* (fab.).

To determine yield, complete-block trials using four replications of 'Bienville' and 'Beauregard' each were conducted at two different Louisiana Agricultural Experiment Station locations, the Burden Research Plantation in Baton Rouge, La. in 2000, and the Sweet Potato Research Station in Chase, La. in 1997. 'Bienville' and 'Beauregard' were both transplanted in randomized complete-block trials at 31, 36, and 41 cm spacings in Loring silt loam soil at the Burden Research Plantation, and at 31 cm spacings in Gilbert silt loam soil at the Sweet Potato Research Station. Each block/plot was fertilized with 250 pounds per acre of nitrogen, $P_2O_5$, and $K_2O$ (about 250 pounds per acre of 13% N, 13% $P_2O_5$, and 13% $K_2O$, 13-13-13 mixed fertilizer). 'Bienville' was compared to 'Beauregard' at early and middle transplanting dates at each location beginning around May or June. Average yields were measured for the following grades of roots: U.S. #1 (51–89 mm in diameter, 76–229 mm long); Canner (25–51 mm in diameter, 51–178 mm long); and Jumbo (larger than U.S. #1 in diameter, length or both, and without objectionable defects). A typical marketable root of 'Bienville' has a length of 130–140 mm, a diameter of 60–70 mm, and a shape that is mostly round-elliptic. The base or distal end of 'Bienville' tends to be more elongated, while the apex or proximal end is slightly rounder. U.S. #1 roots weigh between 150 to 190 g.

Early transplanting date trials were conducted at the Burden Research Plantation. 'Bienville' and 'Beauregard' were transplanted on June 13, and harvested on October 11 (120 days after planting). Producers usually consider 110 to 125 days a typical development period between planting and harvesting. (Variability occurs due to weather conditions.) Average yields, measured as $Mg \cdot ha^{-1}$, are shown in Table 2.

TABLE 2

| Selection (spacing, in cm) | US#1† | Canners† | Jumbos† | TMY† |
|---|---|---|---|---|
| 'Bienville' (41) | 16.3b | 8.0a | 0.2c | 24.4b |
| 'Bienville' (36) | 22.7a | 7.0ab | 1.9bc | 31.5a |
| 'Bienville' (31) | 21.4ab | 7.3ab | 1.1bc | 29.8ab |
| 'Beauregard' (41) | 22.4a | 5.3b | 4.0ab | 31.7a |
| 'Beauregard' (36) | 22.8a | 6.4ab | 5.6a | 34.8a |
| 'Beauregard' (31) | 25.1a | 6.8ab | 4.2ab | 36.0a |
| Least Significant Difference LSD (P < 0.05) | 5.6 | 2.1 | 3.0 | 6.3 |

†Average yields of varieties followed by a common letter do not differ significantly (P < 0.05) according to Duncan's Multiple Range Test.
TMY = total marketable yield Middle transplanting date trials were also conducted at the Burden Research Plantation. 'Bienville' and 'Beauregard' were transplanted on June 22, and harvested on October 27 (127 days after planting). Average yields ($Mg \cdot ha^{-1}$) of 'Bienville' and 'Beauregard' are shown in Table 3.

TABLE 3

| Selection (Spacing, in cm) | US#1† | Canners† | Jumbos† | TMY† |
|---|---|---|---|---|
| 'Bienville' (41) | 17.4a | 5.9ab | 5.7a | 29.0ab |
| 'Bienville' (36) | 16.7a | 4.6ab | 3.6a | 24.9ab |
| 'Bienville' (31) | 14.4a | 5.7ab | 0.9a | 21.0ab |
| 'Beauregard' (41) | 7.6a | 4.7ab | 4.6a | 16.9b |
| 'Beauregard' (36) | 14.2a | 3.3b | 4.1a | 21.6ab |
| 'Beauregard' (31) | 17.1a | 13.4a | 7.9a | 38.5a |
| Least Significant Difference LSD (P < 0.05) | 7.5 | 7.0 | 6.1 | 15.5 |

†Average yields of varieties followed by a common letter do not differ significantly (P < 0.05) according to Duncan's Multiple Range Test.
TMY = total marketable yield Early transplanting date trials were also conducted at the Sweet Potato Research Station. 'Bienville' was transplanted on May 16, and harvested on September 2 (109 days after planting). ('Beauregard' was not included in this transplanting trial.) Average yields ($Mg \cdot ha^{-1}$) by grade are shown in Table 4.

TABLE 4

| Selection (spacing, in cm) | US#1† | Canners† | Jumbos† | TMY† |
|---|---|---|---|---|
| 'Bienville' (31) | 25.8a | 15.2a | 4.8a | 45.7a |
| 'Beauregard' (31) | 25.8a | 11.5a | 6.4a | 45.6a |
| Least Significant Difference LSD (P < 0.05) | 6.2 | 6.0 | 4.9 | 5.8 |

†Average yields of varieties followed by a common letter do not differ significantly (P < 0.05) according to Duncan's Multiple Range Test.
TMY = total marketable yield Middle transplanting date trials were also conducted at the Sweet Potato Research Station. 'Bienville' and 'Beauregard' were transplanted on June 13, and harvested on October 7 (116 days after planting) using a 31 cm spacing. Average yields ($Mg \cdot ha^{-1}$) by grade are shown in Table 5.

TABLE 5

| Selection (spacing, in cm) | US#1† | Canners† | Jumbos† | TMY† |
|---|---|---|---|---|
| 'Bienville' (31) | 26.4b | 14.3a | 2.5a | 43.2b |
| 'Beauregard' (31) | 35.9a | 12.6a | 8.1a | 56.5a |
| Least Significant Difference LSD (P < 0.05) | 7.9 | 4.1 | 6.4 | 9.3 |

†Average yields of varieties followed by a common letter do not differ significantly (P < 0.05) according to Duncan's Multiple Range Test.
TMY = total marketable yield As shown in Tables 2–5, 'Bienville' produced yields comparable to those of 'Beauregard' at early transplanting dates (95% of 'Beauregard' for U.S. #1 grade; 89% of 'Beauregard' for total marketable yield). Spacing had no significant effect on yield. At later planting dates, 'Bienville' had yields slightly less than those of 'Beauregard' at the Sweet Potato Research Station, but were still competitive. Replicated plots on sweetpotato production farms have not shown any predisposition of 'Bienville' to low yield in late plantings. 'Bienville' had harvestable roots approximately 110 days after planting. This represents a typical fleshy root development time in sweetpotatoes.

'Bienville' produces plants (sprouts) one week later than 'Beauregard', in a quantity of approximately 30 to 40% less than 'Beauregard'. Days to harvest are similar to 'Beauregard'. Yields for both total and number one grade roots are typically similar to 'Beauregard'; however, yield may sometimes be slightly less than that of 'Beauregard'.

'Bienville's' primary expected use is as a commercial variety produced on land infested with southern root-knot nematode, soil rot, or both.

We claim:

1. A new and distinct variety of *Ipomoea batatas* plant named 'Bienville', as described and illustrated.

* * * * *